United States Patent
Wong et al.

(10) Patent No.: US 6,692,759 B1
(45) Date of Patent: Feb. 17, 2004

(54) METHODS FOR PREPARING AND USING IMPLANTABLE SUBSTANCE DELIVERY DEVICES

(75) Inventors: Corinne Gail Wong, Carlsbad, CA (US); Hung Tao Hsu, Alhambra, CA (US); Ricardo Azevedo Pontes de-Carvalho, Irvine, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 09/894,914

(22) Filed: Jun. 28, 2001

Related U.S. Application Data

(60) Provisional application No. 60/215,731, filed on Jun. 28, 2000.

(51) Int. Cl.$^7$ .............................. A61F 2/02; A61F 2/14; B32B 15/02
(52) U.S. Cl. .................. 424/423; 424/424; 424/426; 424/427; 424/428; 424/433; 428/402
(58) Field of Search .................. 424/423, 424, 424/426, 427, 428, 433; 428/402

(56) References Cited

U.S. PATENT DOCUMENTS

| | | | |
|---|---|---|---|
| 4,997,652 A | * | 3/1991 | Wong |
| 5,164,188 A | * | 11/1992 | Wong |
| 5,443,505 A | * | 8/1995 | Wong et al. |
| 5,632,984 A | * | 5/1997 | Wong et al. ............ 424/85.4 |
| 5,766,242 A | * | 6/1998 | Wong et al. |
| 5,824,072 A | * | 10/1998 | Wong |
| 5,869,079 A | * | 2/1999 | Wong et al. |
| 6,312,708 B1 | * | 11/2001 | Donovan .................. 424/423 |

* cited by examiner

*Primary Examiner*—Carlos A. Azpuru
(74) *Attorney, Agent, or Firm*—Robert D. Buyan; Stout, Uxa, Buyan & Mullins, LLP.

(57) ABSTRACT

Method for preparing an implantable device for a sustained delivery of a substance within a body of a human or an animal subject, the method including; dissolving a biocompatible polymer in a suitable solvent solution to produce a polymer-solvent solution; adding the substance to the polymer-solvent solution to produce a polymer-solvent solution-substance admixture; drying the polymer-solvent solution-substance admixture to form a substantially dry mass; and one or more of the following three steps:

(1) adding a second polymer-solvent solution-substance admixture to the dry mass and this second polymer-solvent solution-substance admixture is then allowed to dry; and/or, (2) refrigerating the mass; and/or, (3) adding a liquid to the mass to cause the mass to soften and thereafter manipulating the softened mass to a desired shape.

34 Claims, 2 Drawing Sheets

METHODS FOR PREPARING AND USING IMPLANTABLE SUBSTANCE DELIVERY DEVICES

RELATED APPLICATIONS

This application claims priority to U.S. Provisional Application Serial No. 60/215,731 filed on Jun. 28, 2000, the entirety of which is expressly incorporated herein by reference.

FIELD OF THE INVENTION

The present invention relates generally to a) implantable drug delivery devices, b) medical treatment methods and c) experimental animal models useable in biomedical research. More particularly, the present invention relates to new methods of preparing implantable substance delivery pellets and to the use of such pellets to deliver therapeutic agents, biological factors, gene therapy preparations, and other substances for therapeutic purposes or to induce a disease or disorder in laboratory animals.

BACKGROUND OF THE INVENTION

Implantable Substance Delivery Systems

Implantable drug delivery devices have heretofore been known in the art. Such implantable drug delivery devices include pellets, capsules and rods made of porous polymeric material that contains the drug that is to be administered. The device is surgically implanted in the body of a human or veterinary patient and the drug then escapes from the device through pores in the polymer. These types of implantable drug delivery apparatus are particularly useable for delivering drugs at sustained rates over extended periods of time. Examples of drug delivery implants of this type include Norplant®, Lupron Depot® drug-delivery system (TAP Pharmaceutical Products Inc.; Lake Forest, Ill.) and Gliadel Wafer® (Guilford Pharmaceuticals Inc.; Baltimore, Md.).

Use of Implantable Substance Delivery Devices In Animal Models of Disease:

Implantable delivery devices may also be used to deliver bioactive compounds that will induce or mimic a certain disease or disorder in laboratory animals. In one such laboratory animal model, pellets made of polymethylmethacrylate (Hydron NCC non-adhesive cell culture media, from Hydro Med Sciences, 8 Cedar Brook Drive, Cranbury, N.J. 08512333) were prepared to contain substance(s) known to cause retinal neovascularization (e.g., VEGF and/or basic-FGF) and were implanted intravitreally in the eyes of alaboratory animals in an effort to induce experimental retinal neovascularization in the animals. An example of this has been reported in Ozaki, H. et al., Intravitreal Sustained Release VEGF Causes Retinal Neovascularization in Rabbits and Breakdown of the Blood-Retinal Barrier in Rabbits and Primates, Exp. Eye Res. 64:505–517 (1997). However, the materials and methods by which such delivery devices were prepared is less than optimal for all applications or for routine usage of the technique as an animal model for retinal neovascularization in ophthalmologic experimentation. For example, the method of Ozaki et al. does not cause robust neovascularization to occur in subject test animals. In particular, onset of neovascularization does not occur for 2–3 weeks after the implantation procedure. In addition, the neovascularization effect is mild and has a very short lived and reversible effect. Therefore, it is desirable to develop improved materials and methods whereby such implantable devices may be prepared containing not only VEGF, but other factors known to play a role in inducing neovascularization (e.g., basic fibroblast growth factor (bFGF)), or for providing more highly effectctive, sustained delivery of other substances, proteins or therapeutic agents.

New animal models that involve delivery of bological factors that cause neovascularazation (VEGF and/or bFGF) into the eyes of experimental animals are worthy of investigation in view of the seriousness of some of the ophthalmological diseases and disorders characterized by neovascularization. Among these diseases and disorders are diabetic retinopathy and age related macular degeneration (AMD).

Diabetic Retinopathy:

Two main types of diabetic retinopathy are known to occur. The first, "background diabetic retinopathy" or "non-proliferative retinopathy," typically occurs in the earlier stages of diabetic disease. Background diabetic retinopathy is characterized by damage to small retinal blood vessels, causing them to leak blood or fluid into the retina. The loss of vision that occurs as a result of background diabetic retinopathy is typically due to the accumulation of fluid in the central area of the retina, known as the macula. This accumulation of fluid is called macular edema, and can cause temporary or permanent decreased vision.

The second type of diabetic retinopathy is called "proliferative diabetic retinopathy." Proliferative diabetic retinopathy is the end result of the closure or occlusion of many small retinal blood vessels. The retinal tissue, which depends on those vessels for oxygen and nutrition, ceases to function properly and the areas of the retina in which the blood vessels have closed then foster the growth of many new abnormal new blood vessels. This neovascularization process can be very damaging because it can cause intravitreal hemorrhage, formation of retinal scar tissue, retinal detachment and/or glaucoma, any of which can cause substantial vision loss or even blindness.

Diabetic retinopathy can occur in both Type I diabetics (onset of diabetes prior to age 40) and Type II diabetics (onset after age 40), although it tends to be more common and more severe in Type I patients. Because Type II diabetes is often not diagnosed until the patient has had the disease for many years, diabetic retinopathy may be present in a Type II patient at the time diabetes is discovered. In fact, many patients first learn that they have diabetes when their ophthalmologist finds diabetic retinopathy on a routine eye exam.

The duration of diabetes is important in the development of diabetic retinopathy. The longer a patient has had diabetes, the more likely they are to have diabetic retinopathy. Diabetic retinopathy does not usually occur for at least 3 years after the onset of Type I diabetes. After having diabetes for 15 years, however, about 80% of type I diabetics will have some degree of diabetic retinopathy, and 50% will have proliferative retinopathy.

The diagnosis of diabetic retinopathy is made based on the appearance of the retina as seen on a dilated retinal examination. Significant vision-threatening diabetic retinopathy can be present even if you have no visual symptoms. Retinal photographs and fluorescein angiography are also used to diagnose and document progression of diabetic retinopathy. Fluorescein angiography is a technique which involves injecting a dye (fluorescein) into the veins and taking a series of photographs of the retina while the dye circulates through the retinal vessels. This angiography is used to determine which retinal vessels are leaking, and helps direct laser treatment more precisely.

The treatment of diabetic retinopathy in any particular case depends upon multiple factors, including the type and degree of retinopathy, associated ocular factors such as cataract or vitreous hemorrhage, and the medical history of the patient. Treatment options include laser photocoagulation, cryotherapy (freezing), and vitrectomy surgery (removal of the vitreous gel along with blood, scar tissue, etc.)

Age Related Macular Degeneration:

Age-related macular degeneration (AMD) is the largest cause of severe and permanent vision loss in the western world. AMD is primarily an age related disease process although certain individuals are believed to be genetically predisposed to the disease and chronic sunlight exposure and poor nutrition may also be predisposing factors. AMD most commonly occurs after 50 years of age and its occurrence increases in frequency as the population ages.

There are two basic types of age-related macular degeneration—dry and wet. In dry macular degeneration, aging yellow spots called "drusen" are present with or without atrophy of the macula. In this dry form of the disease, the ptient's visual acuity is usually not drastically affected. In the wet form of the disease, abnormal blood vessels grow behind the retina in the subretinal space and leakage of blood and fluid occurs (hence the name "wet"). With time, the abnormal blood vessels proliferate and grow into a scar. Once a scar has formed, the condition is no longer treatable. Only about 10–20% of AMD patients have the wet form of the disease, but the wet form of the disease is responsible for approximately 90% of severe vision loss from AMD.

SUMMARY OF THE INVENTION

The present invention provides new and improved methods for preparing and using substance delivery devices for sustained delivery of substances into a human or animal body. In many instances, the present methods provide substantial benefits. For example, the implantable substance delivery devices of the present invention provide sustained and effective delivery of substances to tissues adjacent the location at which the devices are implanted.

In accordance with the present invention, there is provided methods for preparing an implantable device for a sustained delivery of a substance within a body of a human or animal subject are featured. In these methods, a biocompatible polymer is dissolved in a suitable solvent solution to produce a polymer-solvent solution admixture. Further, a substance is added to the polymer-solvent solution admixture. Still further, the polymer-solvent solution-substance is dried to form a substantially dry mass. The substantially dry mass is refrigerated. In one embodiment, after forming the substantially dry mass and before refrigerating the mass, a liquid is added to the substantially dry mass causing the mass to soften and the softened mass may be manipulated to a desired shape. In one embodiment, a second polymer-solvent solution-substance admixture may be added to the substantially dry mass. This second polymer-solvent solution-substance admixture is allowed to dry. This second polymer-solvent solution-substance admixture may be prepared in the same manner as the afore described polymer-solvent solution-substance admixture. The second polymer-solvent solution-substance admixture may be added to the substantially dry mass before the steps of adding a liquid, manipulating and refrigerating of the mass.

Further in accordance with the present invention, methods for preparing an implantable device for a sustained delivery of a substance within a body of a human or animal subject are featured. In these methods, a biocompatible polymer is dissolved in a suitable solvent solution to produce a polymer-solvent solution admixture. Further, a substance is added to the polymer-solvent solution admixture. Still further, the polymer-solvent solution-substance is dried to form a substantially dry mass. A liquid is then added to the substantially dry mass causing the mass to soften and the softened mass is manipulated to a desired shape. In one embodiment, the manipulated mass may be refrigerated. In one embodiment, a second polymer-solvent solution-substance admixture may be added to the substantially dry mass. This second polymer-solvent solution-substance admixture is allowed to dry. This second polymer-solvent solution-substance admixture may be prepared in the same fashion as the afore described polymer-solvent solution-substance admixture. The second polymer-solvent solution-substance admixture may be added to the substantially dry mass before the steps of adding a liquid, manipulating and refrigerating of the mass.

Still further in accordance with the present invention, methods for preparing an implantable device for a sustained delivery of a substance within a body of a human or animal subject are featured. In these methods, a biocompatible polymer is dissolved in a suitable solvent solution to produce a polymer-solvent solution admixture. Further, a substance is added to the polymer-solvent solution admixture. Still further, the polymer-solvent solution-substance is dried to form a substantially dry mass. Still further, a second polymer-solvent solution-substance admixture is added to the substantially dry mass. This second polymer-solvent solution-substance admixture is allowed to dry. This second polymer-solvent solution-substance admixture is prepared in the same fashion as the afore described polymer-solvent solution-substance admixture. In one embodiment, a liquid may be added to the substantially dry mass causing the mass to soften and the softened mass may be manipulated to a desired shape. In one embodiment, the substantially dry mass may be refrigerated.

Still further in accordance with the invention, the polymers may be non-biodegradable. For example, Hydron (polymethylmethacrylate available commercially as "Hydron NCC" non-adhesive cell culture media, from Hydro Med Sciences, 8 Cedar Brook Drive, Cranbury, N.J. 08512333), polyester, polycarbonate, polysulfone, polyvinyl chloride, polyethylene, polypropylene, poly(N-vinyl pyrrolidone), poly(methyl methacrylate), poly(vinyl alcohol), poly(acrylic acid), polyacrylamide, poly(ethylene-co-vinyl acetate), poly(methacrylic acid), mixtures thereof and combinations thereof may be used.

Still further in accordance with the invention, the polymers may be biodegradable. For example, poly (ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate) poly(bisphenol A iminocarbonate) polycyanoacrylate, polyphosphazene, mixtures thereof and combinations thereof may be used in accordance with the invention.

Still further in accordance with the invention, the solvent solution may comprise an organic solvent. For example, the organic solvent may be ethanol. Ethanol may be used at a concentration of, for example, about 70 to about 95% .

Still further in accordance with the invention, the substance may be a chemical, a therapeutic agent, a biomolecule, a therapeutic biomolecule, an anti-inflammatory agent, an antineoplastic agent, a protein, a steroid, a hormone, a RNA, a DNA, a combination of a RNA and a DNA, an antisense oligonucleotide sequence, an antisense oligoribonucleotide sequence, a combination of an antisense oligonucleotide sequence and an antisense oligoribonucleotide sequence, an antisense oligonucleotide sequence to a focal adhesion kinase RNA, an antisense oligoribonucleotide sequence to a focal adhesion kinase RNA, a combination of an antisense oligonucleotide sequence and an antisense oligoribonucleotide sequence to a focal adhesion kinase RNA, an antisense oligonucleotide sequence to a focal adhesion kinase gene, an antisense oligoribonucleotide sequence to a focal adhesion kinase gene, a combination of an antisense oligonucleotide sequence and an antisense oligoribonucleotide sequence to a focal adhesion kinase gene, VEGF and bFGF.

Still further in accordance with the invention, is a method of using the implantable device by introducing the device into a body of a human or animal subject such that the substance may be released from the device. For example, the device may be implanted into an eye, into the vitreous of an eye by surgical means and into the subchoroidal space where a sclera is cut to expose a choroidae.

Still further in accordance with the invention, is a method where introducing the device into a body of a subject causes a therapeutic benefit to occur.

Still further in accordance with the invention, is a method where a desired disease or disorder is caused in an animal by introducing the device into a body of the animal. For example, the disease or disorder may be neovascularization and/or age-related macular degeneration.

Still further in accordance with the invention, are implantable devices prepared for a sustained delivery of a substance within a body of a human or animal subject made by the afore described methods.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

Figure 1:
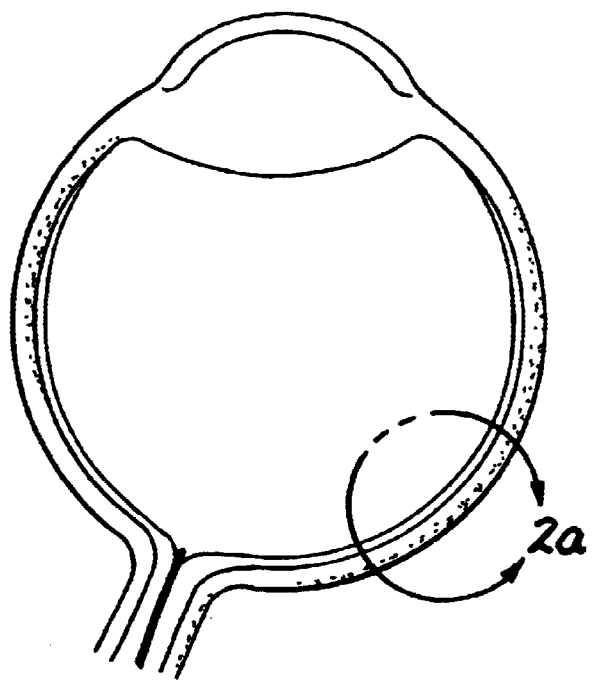
FIG. 1 shows in flow chart form an exemplary method for making a substance delivery device of the present invention comprising VEGF, bFGF and Hydron.

The present invention relates to methods for making and using implantable substance delivery devices. The substance delivery devices are useful to deliver an effective amount of a substance into a body or body part of an animal or human subject.

The substance delivery devices may comprise one or more polymers. Characteristics of the polymers may include biocompatibility, compatibility with the substance of interest, not causing significant increase in viscosity of the vitreous, and like beneficial characteristics.

The polymers may include a combination of hydrocarbons, oxygen and nitrogen. The oxygen may be present as oxy, for example, hydroxy or ether, carbonyl, for example, non-oxo-carbonyl, such as carboxylic acid ester, and the like. The nitrogen may be present as amide, cyano or amino.

The polymeric compositions may be organic polymers. For example, anhydrides, amides, orthoesters and the like, by themselves or in combination with other monomers, may be used to form the polymers. The polymers may be addition or condensation polymers. The polymers may be crosslinked or non-cross-linked.

The polymers may be non-biodegradable. Examples of non-biodegradable polymers that are usable in accordance with the present invention are Hydron, polyester, polycarbonate, polysulfone, polyvinyl chloride, polyethylene, polypropylene, poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid). In a preferred embodiment, Hydron is used (polymethylmethacrylate available commercially as "Hydron NCC" non-adhesive cell culture media, from Hydro Med Sciences, 8 Cedar Brook Drive, Cranbury, N.J. 08512333).

In a particularly advantageous embodiment of the invention, biodegradable polymers are used. These polymers may be subject to enzymatic or hydrolytic degradation within a human or animal body. The degree of stability of the biodegradable polymers can be varied widely. Stability can depend on factors which include choice of monomer, whether a homopolymer or copolymer is employed, whether mixtures of polymers are employed, where the polymers are employed as varying layers or are mixed.

By employing a biodegradable polymer, particularly one where the biodegradation is relatively slow, the rate of release of the substance may be primarily diffusion controlled, depending upon the polymer structure, rather than breakdown of the polymer. The selected polymers may have lifetimes at least equal to the desired period of administration, preferably at least twice the desired period of administration, and may have lifetimes many times the desired period of administration. In one embodiment, the period of administration will be at least 1 day. In another embodiment the period of administration will be at least 5 days. In another embodiment, the period of administration will be at least about 15 days and may be 20 days or more.

Examples of biodegradable polymers that are usable in accordance with the present invention are poly (ethylene glycol), polyvinylpyrrolidine, polyanhydrides polyorthoesters, polyglycolides (PGA), polylactides (PLA), for example poly(d,1-lactide), poly(lactide-co-glycolides) (PLGA), for example pol(d,1-lactide-co-glycolide), polydioxanone, polyanhydride, trimethyl carbonate, poly(beta-hydroxybutyrate), poly(g-ethyl glutamate), poly(DTH iminocarbonate), poly(bisphenol A iminocarbonate), polycyanoacrylate, polyphosphazene, modified polysaccharides, for example cellulose, chitin and dextran, and modified proteins, for example fibrin and casein.

Composition of the delivery devices may be substantially homogeneous or heterogeneous. Thus, devices can be prepared where the center may be of one material and the surface may have one or more layers of the same or different composition. The layers may be cross-linked, of different molecular weight, density, porosity, or the like.

The delivery devices are formulated to include one or more substances which may be released over an extended period of time at an effective dosage into a body of an animal or human subject. In a preferred embodiment, the delivery device is used to release a substance or substances into the interior of an eye. In this embodiment, substances released from delivery devices can reach various regions of the eye including the choroidea, retina, and vitreous.

Diffusion of the substance may be controlled so that delivery is precise. For example, when a delivery device is implanted in the eye, delivery of a substance to primarily the underlying choroidea can be achieved by appropriately setting the concentration of the substance in the delivery device. By increasing the concentration, the substance may diffuse into the retina and/or the vitreous. Thus, the substance can be made available and maintained at an effective dosage where the substance is needed. This, opposed to being quickly washed out as is typically the case with intraocular injection of a substance. Or, as in the case of systemic administration, requiring greatly elevated levels of substance administration to the host to achieve an effective substance concentration level in the eye.

The amount of substance employed in a delivery device may vary widely depending on the effective dosage of the substance and rate of release desired. In one embodiment, the amount of substance will be from about 0.00001% to about 1% of the substance delivery device. In another embodiment, the amount of substance will be from about 1% to about 80% percent of the delivery device. In another embodiment, the amount will be about 10% to about 50% percent of the device.

Any substance for which sustained release is desired may be employed in the present invention. The substances may be capable of diffusion into the body to be present at an effective dose. Substances may be sufficiently soluble to be presented at pharmacologically effective doses. Substances may be in any form. For example, the substances may be in the form of a salt, an acid or a base or combination thereof. Also, the substances may be modified by chemical or other means to facilitate solubility or dispersion of the substances in the delivery device and/or in the body. Some substances which may be employed in the present invention are found in U.S. Pat. No. 4,327,725 which disclosure is incorporated in its entirety herein by reference.

In addition, substances produced by bacteria may be used with the present invention. These bacteria include various acid fast bacilli and Corynebacterium. Substances produced by these and other microorganisms may induce an immune response enhancing immune attack of tumor cells. Substances such as toxins produce by Gram positive and Gram negative bacteria may also be employed in the present invention.

Substances comprising nucleic acid sequences may also be employed with this invention. Examples of nucleic acids that may be employed with the present invention include but are not limited to RNA, DNA and combinations thereof. For example, nucleic acid sequences comprising both ribonucleotides and deoxyribonucleotides. The nucleic acid sequences may be linear or circular molecules. Examples of circular nucleic acids are viruses, plasmids and viral-plasmid fusion vectors. In one embodiment, an antisense nucleotide sequence is used. For example, an antisense oligonucleotide or oligoribonucleotide sequence to a focal adhesion kinase RNA or a focal adhesion kinase gene.

Substances of particular interest for use in accordance with the present invention include protein hormone growth factors, for example, vascular endothelial growth factor (VEGF) and basic fibroblast growth factor (bFGF).

Also of particular interest for use in accordance with the present invention are antioxidants. Examples of antioxidants that may be used in accordance with the present invention are N-acetyl cysteine, glutathione and its esters and L-2-thiazolienone-4-carboxylic acid and its esters.

Other substances of interest for use in accordance with the present invention include hydrocortisone (5 to 20 mcg as plasma level), gentamycin (6 to 10 mcg/ml in serum), 5-fluorouracil (~30 mg/kg bodyweight in serum), sorbinil, IL-2, Phakan-a (a component of glutathione), thiolathiopronin, Bendazac, trifluorothymidine, interferon (alpha, beta and Y), immune modulators, e.g., lymphokines, monokines, and growth factors, cytokines, anti-(growth factors), anti-glaucoma substances, such as the beta-blockers: timolol maleate, betaxolol and metipranolol; mitotics: pilocarpine, acetylcholine chloride, isoflurophate, demacarium bromide, echothiophate iodide, phospholine iodide, carbachol, and physostigimine; epinephrine and salts, such as dipivefrin hydrochloride; and dichlorphenamide, acetazolamide and methazolamide; anti-cataract and anti-diabetic retinopathy substances, such as aldose reductase inhibitors: tolrestat, lisinopril, enalapril, and statil; thiol cross-linking substances other than those considered previously; anti-cancer substances, such as retinoic acid, methotrexate, adriamycin, bleomycin, triamcinolone, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting substances, such as tissue plasminogen activator, urokinase, and streptokinase; anti-tissue damage substances, such as superoxide dismutase; proteins and nucleic acids, such as mono- and polyclonal antibodies, enyzmes, protein hormones and genes, gene fragments and plasmids; steroids, particularly anti-inflammatory or antifibrous substances, such as cortisone, hydrocortisone, prednisolone, prednisone, dexamethasone, progesterone-like compounds, medrysone (HMS) and fluorometholone; cycloplegic and mydriatic substances, such as atropine, cyclogel, scopolamine, homa-tropine mydriacyl, anticholinergics, anticoagulants, antifibrinolytic substances, antihistamines, antimalarials, antitoxins, chelating substances, hormones, immunosuppressives, thrombolytic substances, vitamins, salts, desensitizing substances, prostaglandins, amino acids, metabolites and antiallergenics.

More substances of interest for use in accordance with the present invention include non-steroidal, anti-inflammatory substances, such as acetylsalicylic acid (aspirin), indomethacin, diclofinac, fenoprofin, ketrolac tromethamine, diclofenac sodium and suprofen; antifungal and antimicrobial agents, such as fluoroquinolones, tetracyclines, aminoglycosides, vancomycin, cephlosporins, sulfonamides, loridine (cephaloridine), chloramphenicol, clindamycin, amikacin, tobramycin, methicillin, lincomycin, oxycillin, penicillin, amphotericin B, poly-myxin B, cephalosporin family, ampicillin, bacitracin, carbenicillin, cepholothin, colistin, erythromycin, streptomycin, neomycin, sulfacetamide, silver nitrate, sulfisoxazole and diolamine; other antipathogens, including anti-viral substances, such as idoxuridine, trifluorouridine, vidarabine (adenine arabinoside), acyclovir (acycloguanosine), gancyclovir, pyrimethamine, trisulfapyrimidine-2, clindamycin, nystatin, flucytosine, natamycin, miconazole and piperazine derivatives, e.g. diethylcarbamazine.

Still more substances of interest for use in accordance with the present invention include anti-tumor or chemotherapeutic agents and pharmaceutically acceptable salts thereof, for example: leucovorin, antimetabolites, 6-mercaptopurine, methotrexate, 5-fluorouracil, anthracyclines, doxorubicin, daunorubicin, mitoxantrons. Bleomycin, nitrosoureas (eg. carmustine (BCNU)), procarbazine, vincriotine, thiotepa, fluoxymesterone, vinblastine, etopside, decarbazine, levamisole, irinotecan, mitomicin-C, streptozocin, camptothcen (CPT) drugs, estrogen receptor antagonists, piclitaxei, taxoids, tamoxifen, carboplatin, cisplatin, cyclophosphamide, 4-hydroperoxy-cyclophosphamide, angigenesio inhibitors, heparin-cortisons, minocycline, topoisomerase inhibitor, antimetastatic agents, antiangiogenic agents, antisense oligonucleotides, cytarabine-cytosine arabinoside, dactinomycin, dexamethasone, floxuridine, fluoxymesterone, flutamide, fludarabine, goserelin, hydroxyurea, indarubic-HCl, ifosfamide-isophosphamide, altretamine, asparaginase, busulfan, cladribine, 2-chlorodeoxyadenosine, irinotecan, leuprolide, megestrol, melphalan-L-phenylalanine mustard, L-sarcolysin, MESNA, plicamycin-mithramycin, prednisone, procarbazine, streptozocin-streptozotocin, 6-thioguanine, vinorelbine tartrate and biological cancer theraputic agents such as p53 genes, antibodies, interferons, interlukens, hematopoietic growth factors, tumor necrosis factors and gene therapy agents containing genetic material.

Combination chemotherapy (i.e. two or more chemotherapeutic drugs used in combination) is desirable in the treatment of many types of cancers. The multi-layered implants of the present invention may be particularly useful for delivering two or more substances for use in, for example, combination chemotherapy.

To make the delivery device, solvent-evaporation methods may be employed. In these methods, the biocompatible polymer is dissolved in a liquid which may subsequently be evaporated. The liquid may be a water based liquid. The liquid may be a water-immiscible solvent such as ether, chloroform, benzene or carbon tetrachloride. In addition, the liquid may be a substantially water-miscible solvent. For example, alcohols with carbon backbone length of n=1, n=2, n=3, n=4, n=5, n=6, n=7 and n=8 may be employed. Any liquid suitable to make a substance delivery device in accordance with the present invention is covered by the scope of the invention. In a particularly useful embodiment, an ethanol solvent solution is used. Preferably, the ethanol solution contains 95% ethanol. More preferably, the ethanol solution contains 70% ethanol.

The amount of polymer employed in the liquid may vary depending on the size of the delivery device desired, the viscosity of the solvent solution, the solubility of the polymer and factors of the like. For example, the concentration of polymer may be in the range of about 20% to about 80% percent of the substance delivery device. The ratio of substance to polymer may also vary with the desired rate of release.

The size of the delivery devices may range from a lower size limit defined by the ability to make and use the device to an upper size limit determined by factors such as body tolerance for the delivery device, size limitations on insertion, ease of handling and the like.

The size and form of the delivery device can be used to control the rate of release, substance concentration released into the body and length of treatment.

In one useful embodiment of the invention, the device comprises more than one polymer-substance layer. Initially, in this embodiment, a desired amount of biocompatible polymer is dissolved in a solvent solution. In one embodiment, the polymer is Hydron. Preferably, Hydron powder is used. In one embodiment, an 8% Hydron-solvent solution admixture is used. The dissolving may be done at a temperature found between the freezing point and boiling point of the solvent solution. In a preferred embodiment, the mixing temperature is approximately 25° C. In one embodiment, the dissolving may be done with shaking. In one embodiment, the solvent solution is ethanol. Preferably, the solvent solution is 95% ethanol. More preferably, the solvent solution is 70% ethanol. After dissolving the polymer, the polymer-solvent solution may be mixed with the desired substance. A first substance, for example bFGF, may be dissolved in the polymer-ethanol solution at a temperature from about 4° C. to about 90° C. Shaking may be employed to assist in the dissolving. In one embodiment, the substance is dissolved at 25° C. A volume of the substance-polymer-solvent solution, for example 20 ul, is aliquoted directly into a container. Preferably the container is a small sterile plastic beaker. For example, a 30 ml beaker may be used. The puddle that forms at the bottom of the beaker is allowed to dry substantially to form a layer. The drying temperature may be between about 4° C. to about 100° C. Preferably the drying temperature is about 25° C. Next, a second substance, for example VEGF, may be dissolved in a polymer-solvent solution in a manner that may be similar to that of the substance previously described (e.g. the first substance). A volume of this second substance-polymer-solvent solution, for example 20 ul, is aliquoted carefully onto the top of the substantially dried layer of the first substance-polymer-solvent solution. This second volume is allowed to dry substantially in a manner that may be similar to that of the first to form a two layered mass. This process can be continued with few to many layers of substance being applied to the growing mass. In other embodiments, a single layer mass may be used. Also, the layer(s) may comprise more than one substance. An adequate amount of water is aliquoted onto the top of the dried layers to soften the mass. For example, 15–20 ul of water may be adequate for a two layered mass. The addition of water may soften the dried mass. The softened mass may be manipulated quite easily into a desired shape. In one embodiment, the desired shape is a round pellet, for example, approximately 1–2 mm in diameter. The mass may then be substantially dried. The drying temperature may be between about 4° C. to about 100° C. Preferably the drying temperature is about 25° C. The pellet may then be refrigerated for curing at a temperature of approximately 4° C. The curing may last, for example, from approximately 10 minutes to approximately 120 hours or more. In one embodiment, the refrigeration lasts about 12 hours. In one embodiment, the pellet is rolled gently up the side of the beaker so that it does not sit in the water that is left at the bottom of the container. The pellet may then be allowed to "hang" on the side of the container while curing in the refrigerator. Without wishing to limit the invention to any particular theory of operation, it is believe that when the delivery device is prepared as described, the resulting device takes on a unique layered structure important for effective delivery of the substances to the body, for example, the eye. Steps that are important in producing this effect include 1) producing a layered mass, 2) curing at about 4° C. and 3) moistening and manipulating the mass.

On the day of surgery, the refrigerated mass may be kept in its individual beaker and placed on wet ice until it is ready to be implanted into the body. In this way, the stability of the incorporated proteins within the pellet may be maintained as long as possible. For example, if N=8 pellets are made, then all 8 pellets in their respective beakers may be placed immediately from the refrigerator onto wet ice in a bucket and subsequently transported in this manner to the surgical suite until each eye is suitably prepped for implantation of the mass.

Various components may be employed in the formulation of the delivery devices for a variety of purposes. For example, buffering agents and preservatives may be employed. Examples of water soluble preservatives include DHT, DHA, sodium bisulfite, sodium thiosulfate, ascorbate, benzalkonium chloride, chlorobutanol, thimerosal, phenylmercuric borate, parabens, benzyl alcohol and phenylethanol. These substances may be present in individual amounts of from about 0.001 to about 5% by weight and preferably about 0.01 to about 2%. Suitable water soluble buffering substances are alkali or alkaline earth, carbonates, phosphates, bicarbonates, citrates, borates, acetates, succinates and the like, such as sodium phosphate, citrate, borate, acetate, bicarbonate and carbonate. These substances may be present in amounts sufficient to maintain a pH of the system of between 2 to 9 and preferably 4 to 8. As such the buffering substance may be as much as 5% on a weight to weight basis of the total composition.

Delivery devices prepared in the above-described manner may be introduced into the body of a human or animal subject for the purpose of delivering the substance into the body of the subject. The delivery devices may be introduced into the body in a variety of ways, including, but not limited to, surgical means, injection, trocar, and means of the like.

In one embodiment, the substance delivery device is implanted into an eye. The delivery devices may be implanted into a variety of components of the eye including but not limited to, the macular area, the retina, the sclera, the anterior chamber, the vitreous and the choroidea. For example, the substance delivery device may be surgically implanted into the vitreous of an eye. In a preferred embodiment, the substance delivery device is implanted into the subchoroidal space of an eye. The choroidea can be exposed through a sclerotomy and the delivery device placed in the exposed space on either side of the incision in dimensions commensurate with the size and shape of the subchoroidea space.

Initially, in development of the present invention for induction of choroidal (subretinal) neovascularization, two surgical approaches were assessed for implantation of the substance delivery devices. First, a traditional anterior approach was attempted where a standard vitrectomy was performed; a sub-retinal bleb was created; and then the delivery device was inserted within the bleb into the vitreous by standard operating procedures. This anterior surgical approach resulted in major trauma and hemorrhaging within the globe. Moreover, the surgical procedure was extremely lengthy. Second, a transcleral posterior surgical approach was attempted where a scleral flap was created after three sclerotomies were performed; the scleral flap was pulled gently away from the choroidal vasculature; the pellet was placed gently on the spongy choroid; and then the flap was sutured closed. Although the globe healed nicely, the entire procedure was extremely lengthy and the risk of hemorrhaging was increased from the multiple sclerotomies that were necessary to produce the scleral flap.

Figure 2A:
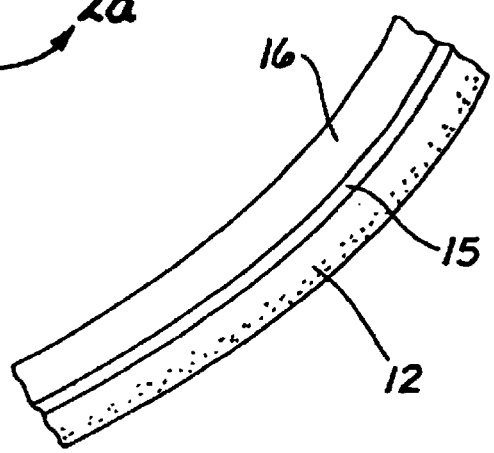
FIGS. 2a–2e shows in step by step fashion a subchoroidal implantation of an implantable drug delivery device usable in accordance with the present invention. The figures show a cross-sectional view of an eye.
Figure 2B:
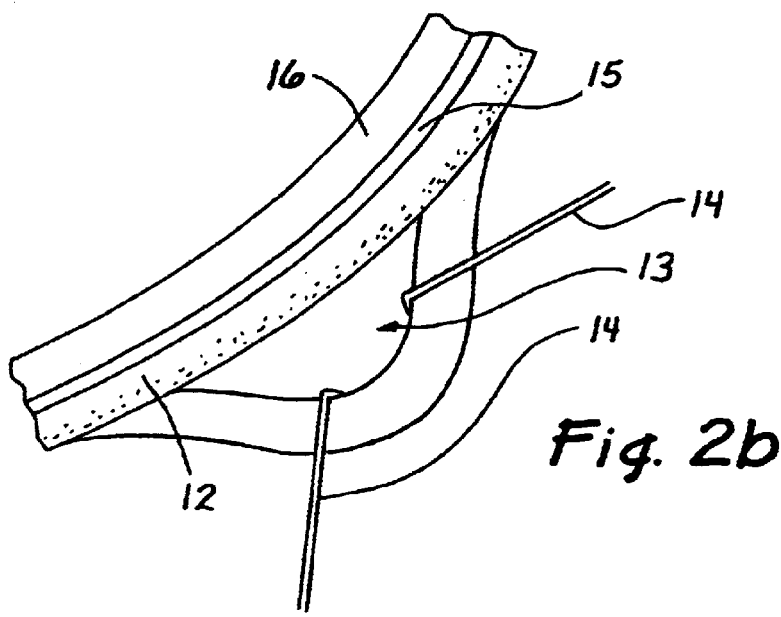
Figure 2C:
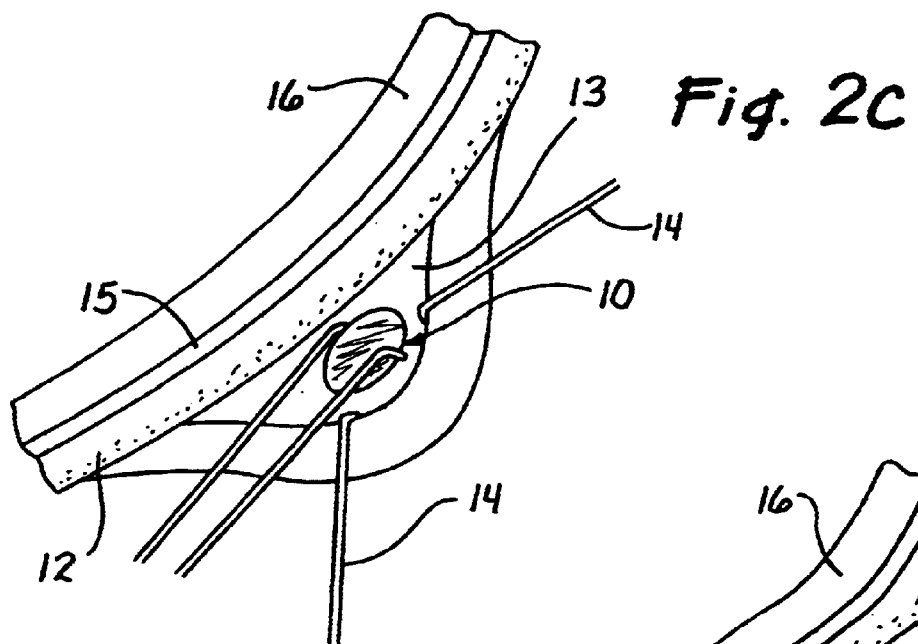
Figure 2D:
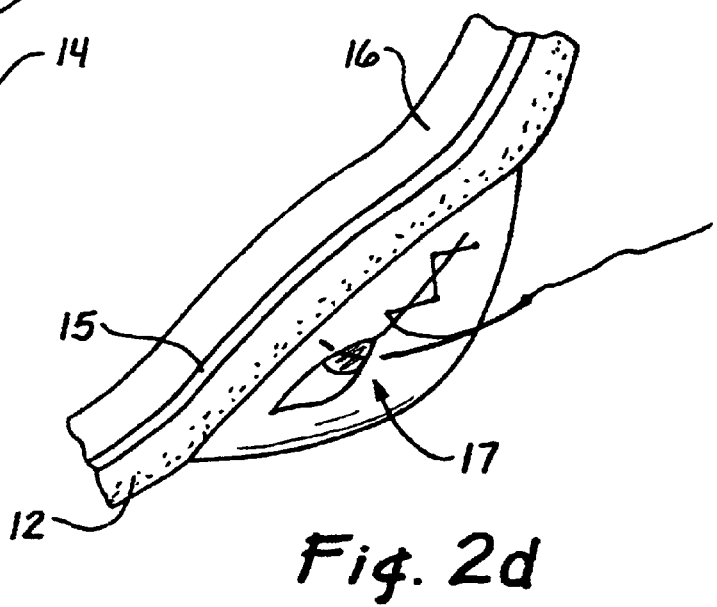
Figure 2E:
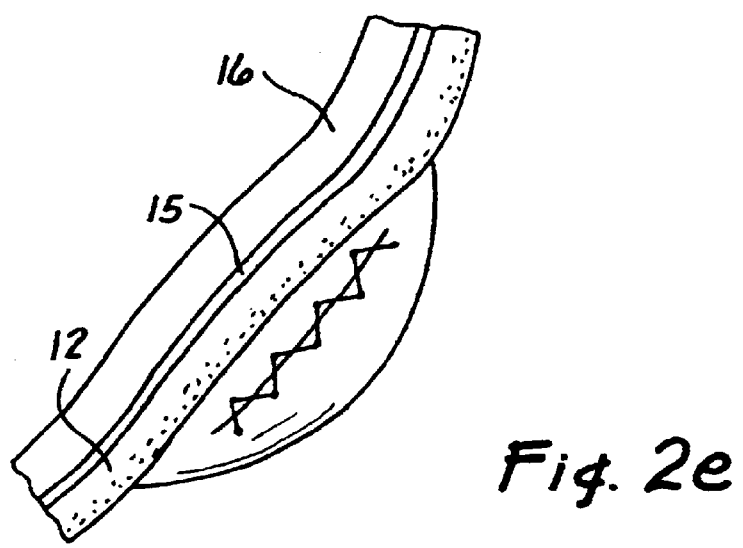

FIGS. 2a–2e show in step-by-step fashion an example of a subchoroidal implantation of a substance delivery device of this invention. As shown, in this example a delivery device 10 that is preferably between about 1.0 to 1.5 mm in diameter and contains either basic fibroblast growth factor (bFGF) or vascular endothelial growth factor (VEGF) alone or a combination of both VEGF and bFGF as a layered mass is implanted subchoroidally. The implantation is performed on pigmented adult Dutch belt rabbits and New Zealand white (NZW) rabbits (N=20). Control animals (N=3) are implanted with blank Hydron pellets. All devices 10 are implanted either nasally or temporally superior to the optic streak through a single sclerotomy. To accomplish this the eye 11 is removed from the socket and held in place outside the socket by forceps or by suturing the eye to tissue of the animal near the socket. An incision in the sclera 11 is made approximately 2 mm in length and a small space or "pocket" 13 is created by gentle manipulation using a surgical device (s) 14 to separate the choroidal sponge-like vasculature 15 which is adjacent to the retina 16 from the outer sclera. The implantation is performed either in the inferior or superior region of the optic disk or streak. Implantation is made in a vicinity in proximity to the major optic streak vasculature. Surgical implantation in the superior region of the eye is easier to perform than implantation in the inferior region. However, implantation in the inferior region provided for an easier post-surgical monitoring of the eye opposed to implantation in the superior region. After implantation and suturing 17 the choroidal pocket closed, the eye is returned to the socket. Negative choroidal and retinal/RPE puncturing is confirmed fundoscopically.

Following surgical pocket implantation of the delivery devices, animals are monitored for between 7 days and 6 weeks by indirect ophthalmolscopy. Fluorescein angiography is also performed. Eyes that are implanted with VEGF/bFGF-containing pellets appeared to develop choroidal neovascularization as determined by clinical observations while eyes implanted with bFGF-containing pellets did not. Such clinical responses included subretinal hemorrhage, exudates, pigment dispersion, and later in the course of the pathology, atrophy of the retinal pigment epithelium (RPE). These clinical observations are very similar to those seen in age-related macular degeneration suggesting this system is an excellent model for the testing of possible therapeutic agents for treatment of AMD.

While this invention has been described with respect to various specific examples and embodiments, it is to be understood that the invention is not limited thereto and that it can be variously practiced with the scope of the following claims.

What is claimed is:

1. A method for preparing an implantable device for a sustained delivery of a chemical substance within a body of a human or an animal subject, said method comprising the steps of:
   (A) dissolving a biocompatible polymer in a suitable solvent solution to produce a polymer-solvent solution;
   (B) adding said chemical substance to said polymer-solvent solution to produce a polymer-solvent solution-substance admixture;
   (C) drying said polymer-solvent solution-substance admixture to form a substantially dry mass; and
   (D) refrigerating said mass.

2. A method according to claim 1 wherein, between steps C and D, said method further comprises:
   adding a liquid to said mass to cause said mass to soften;
   manipulating said softened mass to a desired shape.

3. A method according to claim 1 wherein a second polymer-solvent solution-substance admixture made by steps (A) and (B) is added to said substantially dry mass of said step (C) and said second polymer-solvent solution-substance admixture is allowed to dry.

4. A method according to claim 1 wherein said polymer is non-biodegradable.

5. A method according to claim 4 wherein said non-biodegradable polymer is selected from the group consisting of Hydron, polyester, polycarbonate, polysulfone, polyvinyl chloride, polyethylene, polypropylene, poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), mixtures thereof and combinations thereof.

6. A method according to claim 4 wherein said non-biodegradable, polymer is Hydron.

7. A method according to claim 1 wherein said polymer is biodegradable.

8. A method according to claim 7 wherein said , biodegradable polymer is selected from the group consisting of poly (ethylene glycol), polyvinylpyrrolidine, polylactides (PLA), polyglycolides (PGA), poly(lactide-co-glycolides) (PLGA), polyanhydrides, polyorthoesters, mixtures thereof and combinations thereof.

9. A method according to claim 1 wherein said solvent solution comprises an organic solvent.

10. A method according to claim 1 wherein said solvent solution comprises ethanol.

11. A method according to claim 1 wherein said solvent solution comprises about 70% ethanol.

12. A method according to claim 1 wherein said substance is a therapeutic agent.

13. A method according to claim 1 wherein said substance is a biomolecule.

14. A method according to claim 1 wherein said substance is a therapeutic biomolecule.

15. A method according to claim 1 wherein said substance is an anti-inflammatory agent.

16. A method according to claim 1 wherein said substance is an antineoplastic agent.

17. A method according to claim 1 wherein said substance is a protein.

18. A method according to claim 1 wherein said substance is a steroid.

19. A method according to claim 1 wherein said substance is a hormone.

20. A method according to claim 1 wherein said substance is an RNA, DNA or combination thereof.

21. A method according to claim 1 wherein said substance is an anti-sense oligoribonucleotide sequence, antisense oligonucleotide sequence or a combination thereof.

22. A method according to claim 1 wherein said substance is an anti-sense oligonucleotide, anti-sense oligoribonucleotide or combination thereof to a focal adhesion kinase RNA.

23. A method according to claim 1 wherein said substance is an anti-sense oligonucleotide anti-sense oligoribonucleotide or combination thereof to a focal adhesion kinase gene.

24. A method according to claim 1 wherein said substance comprises VEGF, bFGF or a combination thereof.

25. A method for using an implantable device comprising a step of introducing a device produced according to claim 1 into a body of a human or animal subject such that said substance will be released from said device.

26. A method according to claim 25 wherein said introducing step comprises a step of implanting said device into an eye.

27. A method according to claim 25 wherein said introducing step comprises a step of implanting into a vitreous of an eye by surgical means.

28. A method according to claim 25 wherein said introducing step comprises a step of implanting said device into a subchoroidal space, where a sclera is cut to expose a choroidea.

29. A method according to claim 25 wherein said substance causes a therapeutic benefit to occur in said body of said subject into which said device is implanted.

30. A method according to claim 25 wherein said introducing step causes a desired disease or disorder in said animal so as to provide an animal model for said disease or disorder.

31. A method according to claim 30 wherein said disorder is neovascularization.

32. A method according to claim 30 wherein said disease is age-related macular degeneration.

33. An implantable substance delivery device for a sustained delivery of a substance within a body of a human or an animal subject made by a method according to claim 1.

34. A method according to claim 1 wherein said substance is a chemical.

* * * * *

UNITED STATES PATENT AND TRADEMARK OFFICE
CERTIFICATE OF CORRECTION

PATENT NO. : 6,692,759 B1
DATED : February 17, 2004
INVENTOR(S) : Wong et al.

It is certified that error appears in the above-identified patent and that said Letters Patent is hereby corrected as shown below:

<u>Title page,</u>
Item [56], References Cited, U.S. PATENT DOCUMENTS, please remove the symbol "*" and correct the cited reference to read as follows:

| | | | |
|---|---|---|---|
| -- 4,997,652 A | 3/1991 | Wong | |
| 5,164,188 A | 11/1992 | Wong | |
| 5,443,505 A | 8/1995 | Wong et al. | |
| 5,632,984 A | 5/1997 | Wong et al. | 424/85.4 |
| 5,766,242 A | 6/1998 | Wong et al. | |
| 5,824,072 A | 10/1998 | Wong | |
| 5,869,079 A | 2/1999 | Wong et al. | |
| 6,312,708 B1 | 11/2001 | Donovan | 424/423 -- |

Signed and Sealed this

Twenty-second Day of June, 2004

JON W. DUDAS
*Acting Director of the United States Patent and Trademark Office*